(12) United States Patent
Haley et al.

(10) Patent No.: US 9,773,988 B2
(45) Date of Patent: Sep. 26, 2017

(54) DIINDENOANTHRACENE AND DIINDENOPENTACENE

(71) Applicant: University of Oregon, Eugene, OR (US)

(72) Inventors: Michael M. Haley, Eugene, OR (US); Gabriel Rudebusch, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 15/092,383

(22) Filed: Apr. 6, 2016

(65) Prior Publication Data

US 2016/0301021 A1 Oct. 13, 2016

Related U.S. Application Data

(60) Provisional application No. 62/146,086, filed on Apr. 10, 2015.

(51) Int. Cl.
| | | |
|---|---|---|
| *H01L 51/00* | (2006.01) | |
| *C07F 7/08* | (2006.01) | |
| *H01L 51/05* | (2006.01) | |
| *H01L 51/50* | (2006.01) | |

(52) U.S. Cl.
CPC ........ *H01L 51/0094* (2013.01); *C07F 7/0812* (2013.01); *C07F 7/0818* (2013.01); *H01L 51/0056* (2013.01); *H01L 51/0057* (2013.01); *H01L 51/0558* (2013.01); *H01L 51/5056* (2013.01)

(58) Field of Classification Search
CPC .................................. C07F 7/0812; C07F 7/08
See application file for complete search history.

(56) References Cited

U.S. PATENT DOCUMENTS

| | | |
|---|---|---|
| 6,690,029 B1 | 2/2004 | Anthony et al. |
| 7,385,221 B1 | 6/2008 | Anthony et al. |
| 8,927,117 B2 * | 1/2015 | Buesing ................ C07C 13/62 257/40 |
| 9,099,660 B2 | 8/2015 | Haley et al. |
| 2008/0220285 A1 | 9/2008 | Vestweber et al. |
| 2009/0149627 A1 | 6/2009 | Pan et al. |
| 2013/0096336 A1 | 4/2013 | Haley et al. |

FOREIGN PATENT DOCUMENTS

WO WO 2011/159763 12/2011

OTHER PUBLICATIONS

Chase et al., "Indeno[1,2-b]fluorenes: Fully Conjugated Antiaromatic Analogues of Acenes," *Angew. Chem. Int. Ed.*, 50:1127-1130, 2011.
International Search Report and Written Opinion issued in International Application No. PCT/US2011/040451 on Oct. 14, 2011.
Padwa et al., "A Comparative Study of the Decomposition of o-Alkylnyl-Substituted Aryl Diazo Ketones. Synthesis of Polysubstituted β-Naphthols via Arylketene Intermediates," *J. Org. Chem.*, 58:6429-6437, 1993.
Miyawaki et al., "Multiple Cycloaromatization of Novel Aromatic Enediynes Bearing a Triggering Device on the Terminal Acetylene Carbon," *Tet. Lett.*, 39:6923-6926, 1998.
Rose et al., "Synthesis, Crystal Structures and Photophysical Properties of Electron-Accepting Diethynylindenofluorenediones," *Org. Lett.*, 13:2106-2109, 2011.

\* cited by examiner

*Primary Examiner* — Paul A Zucker
(74) *Attorney, Agent, or Firm* — Klarquist Sparkman, LLP

(57) ABSTRACT

A compound having a structure represented by formula I:

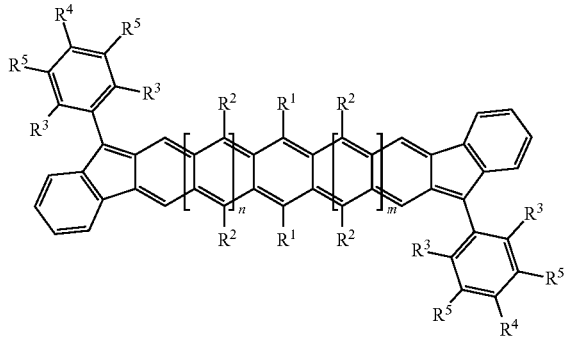

Formula I wherein each $R^1$ is independently H, alkynyl or substituted alkynyl;
each $R^2$ is independently H, alkynyl or substituted alkynyl;
each $R^3$ is independently alkyl or halogen;
each $R^4$ is independently H, alkyl, or halogen;
each $R^5$ is independently H or halogen;
n is 0 or 1; and
m is 0 or 1, provided that if n is 0 then m is 0, and if n is 1 then m is 1.

25 Claims, 12 Drawing Sheets

Steady-state properties of DIAn and OFET device results.

Solid-state structure of DIAn by single crystal X-ray diffraction

Temperature dependent properties of DIAn.

a) variable temperature NMR
b) SQUID measurements
c) variable temperature Raman spectra

Theoretical assessment of DIAn showing the open-shell nature

DIINDENOANTHRACENE AND DIINDENOPENTACENE

This application claims the benefit of U.S. provisional application 62/146,086, filed Apr. 10, 2015, which is incorporated herein by reference.

ACKNOWLEDGEMENT OF GOVERNMENT SUPPORT

This invention was made with government support under Grant No. CHE1301485 awarded by the National Science Foundation. The government has certain rights in the invention.

BACKGROUND

Acenes are an exciting class of compounds that have been intensely studied during the past decade. Their alluring optoelectronic properties suggest great potential as the conducting organic material in a variety of device applications such as organic light-emitting diodes (OLEDs), field-effect transistors (OFETs), and solar cells.

SUMMARY

Disclosed herein are diindenoanthracenes, particularly alkynylated diindenoanthracenes, and diindenopentacenes, particularly alkynylated diindenopentacenes.

Also disclosed herein are electronic or electrooptical devices that include the diindenoanthracenes or diindenopentacenes.

Disclosed herein are compounds having a structure represented by formula I:

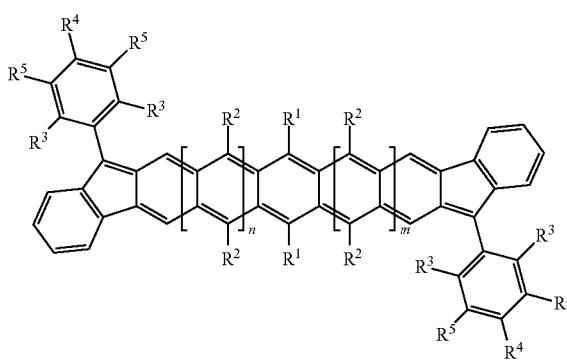

Formula I wherein each $R^1$ is independently H, alkynyl or substituted alkynyl;
each $R^2$ is independently H, alkynyl or substituted alkynyl;
each $R^3$ is independently alkyl or halogen;
each $R^4$ is independently H, alkyl, or halogen;
each $R^5$ is independently H or halogen;
n is 0 or 1; and
m is 0 or 1, provided that if n is 0 then m is 0, and if n is 1 then m is 1.

Further disclosed herein is a compound having a structure represented by formula III:

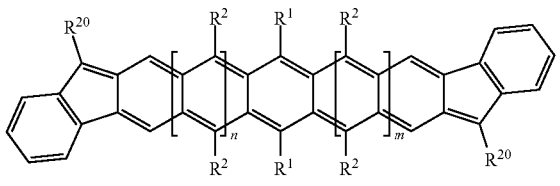

Formula III wherein each $R^1$ is independently H, alkynyl or substituted alkynyl;
each $R^2$ is independently H, alkynyl or substituted alkynyl;
each $R^{20}$ is independently aryl, substituted aryl, heterocyclic, substituted heterocyclic, alkenyl, substituted alkenyl, alkynyl, or substituted alkynyl;
n is 0 or 1; and
m is 0 or 1, provided that if n is 0 then m is 0, and if n is 1 then m is 1.

Also disclosed herein is a compound having a structure represented by formula V:

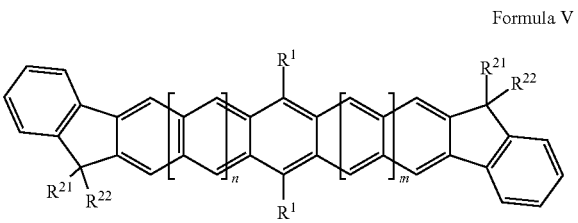

Formula V wherein each $R^1$ is independently H, alkynyl or substituted alkynyl;
each $R^{21}$ and $R^{22}$ is independently aryl, substituted aryl, heterocyclic, or substituted heterocyclic,
n is 0 or 1; and
m is 0 or 1, provided that if n is 0 then m is 0, and if n is 1 then m is 1.

Additionally disclosed herein is a compound having a structure represented by formula VII:

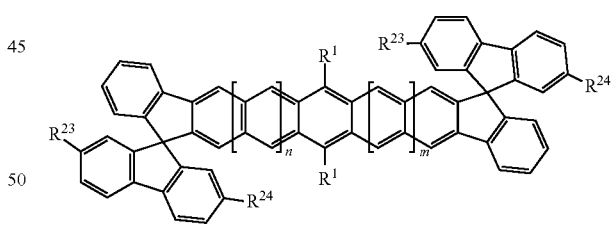

wherein each $R^1$ is independently H, alkynyl or substituted alkynyl;
each $R^{23}$ and $R^{24}$ is independently aryl, substituted aryl, heterocyclic, or substituted heterocyclic,
n is 0 or 1; and
m is 0 or 1, provided that if n is 0 then m is 0, and if n is 1 then m is 1.

The foregoing will become more apparent from the following detailed description, which proceeds with reference to the accompanying figures.

DETAILED DESCRIPTION

Terminology

Figure 1:
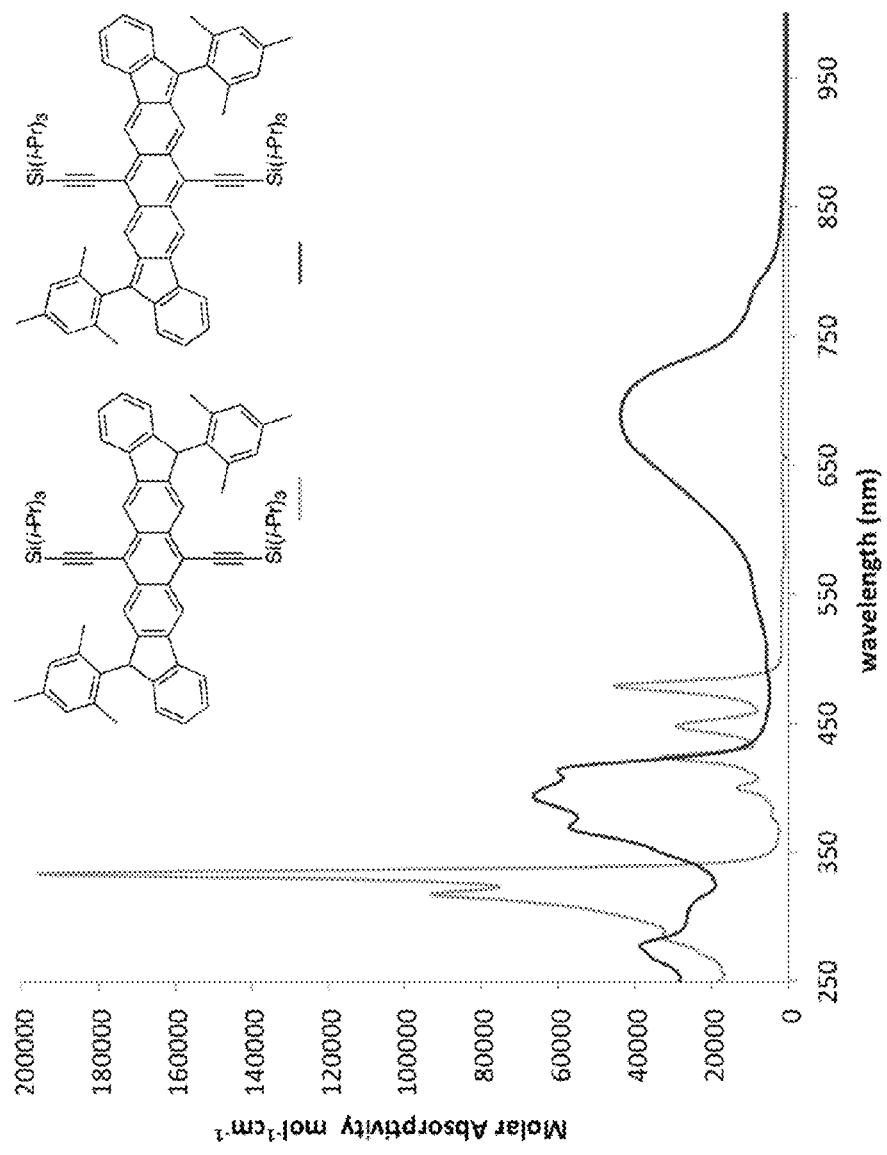
FIG. 1 is adsorption spectra of a novel compound disclosed herein.
Figure 2:
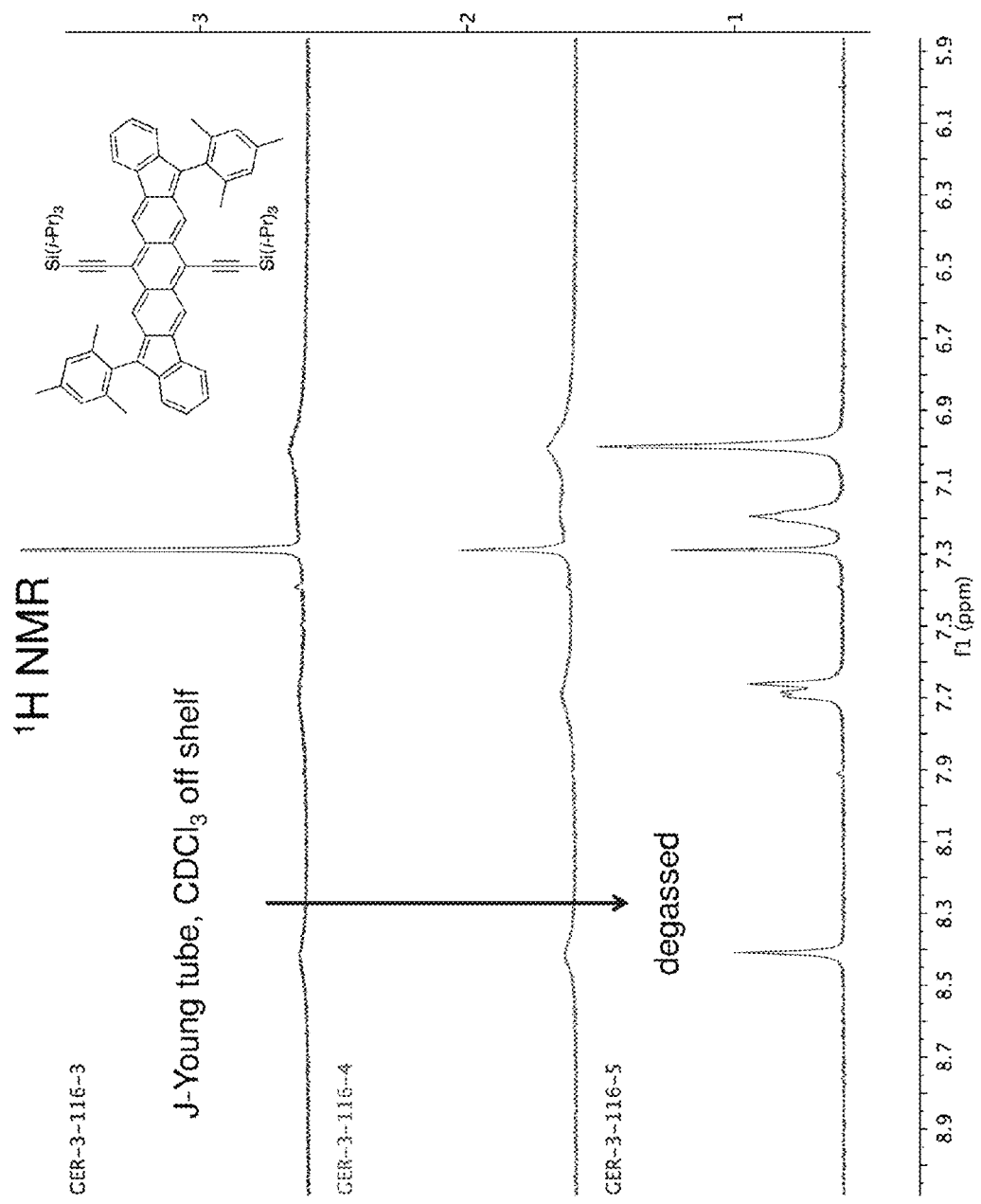
FIG. 2 is $^1$H NMR spectra of a novel compound disclosed herein.
Figure 3:
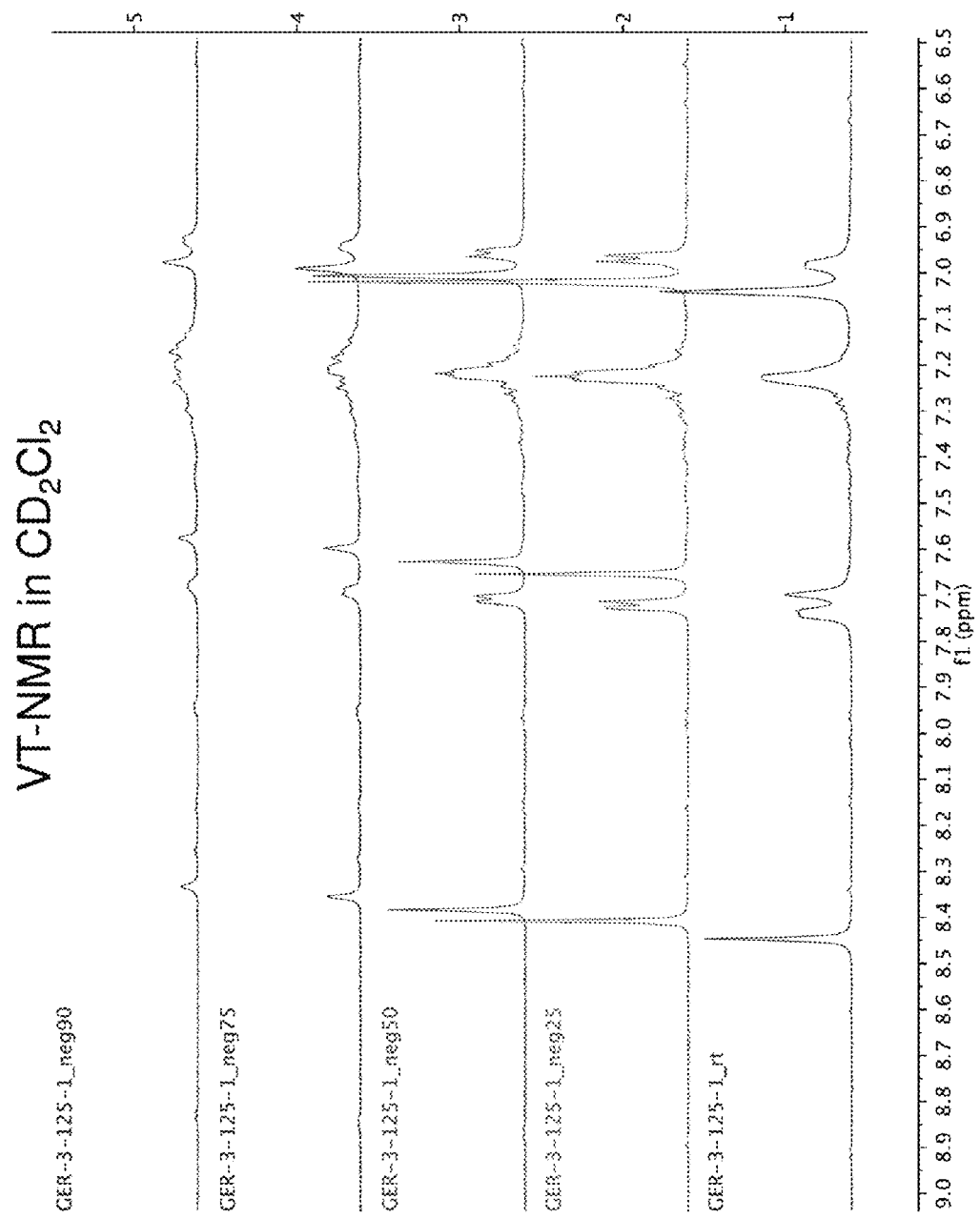
FIG. 3 is VT-NMR spectra of a novel compound disclosed herein.
Figure 4:
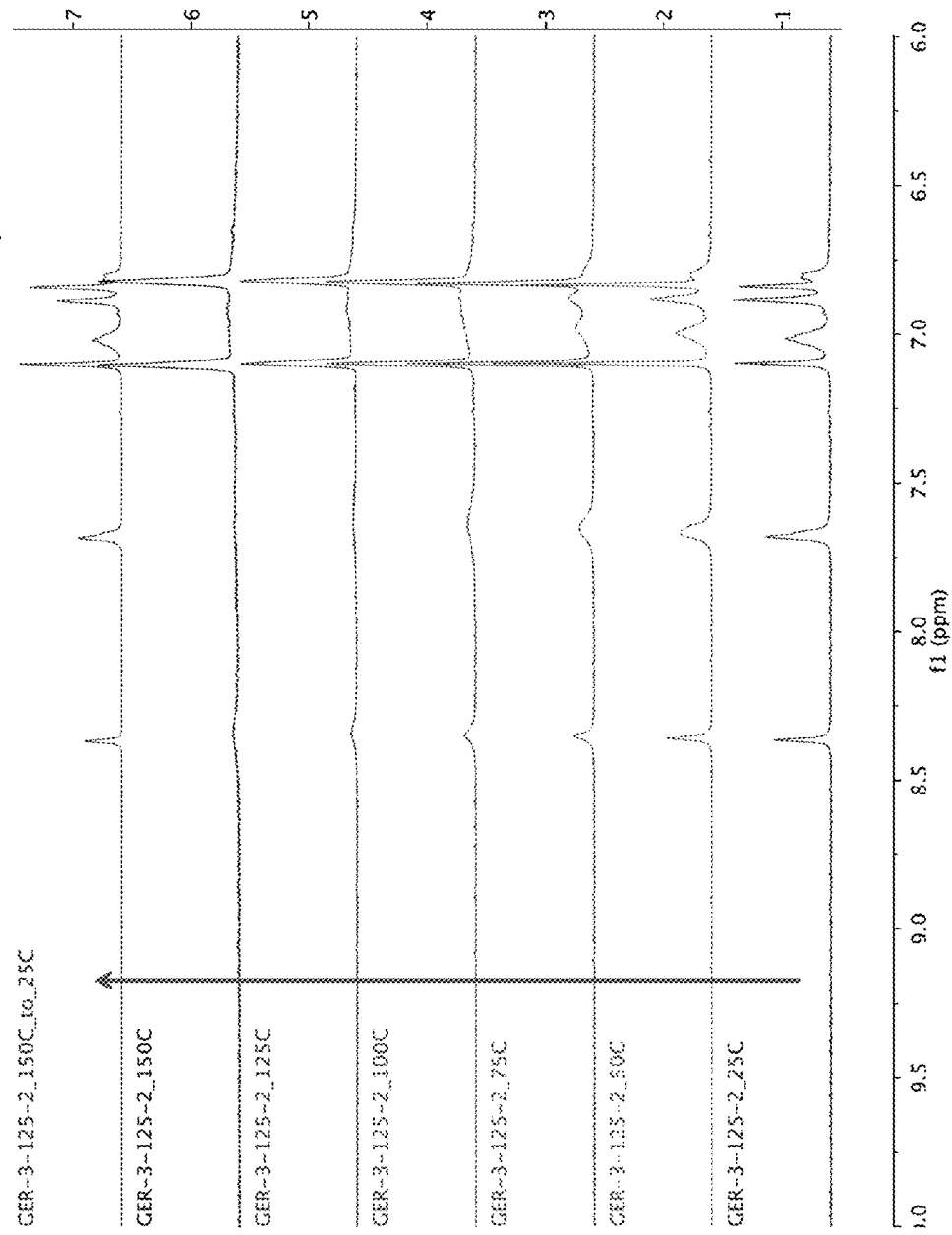
FIG. 4 is VT-NMR spectra of a novel compound disclosed herein.
Figure 5:
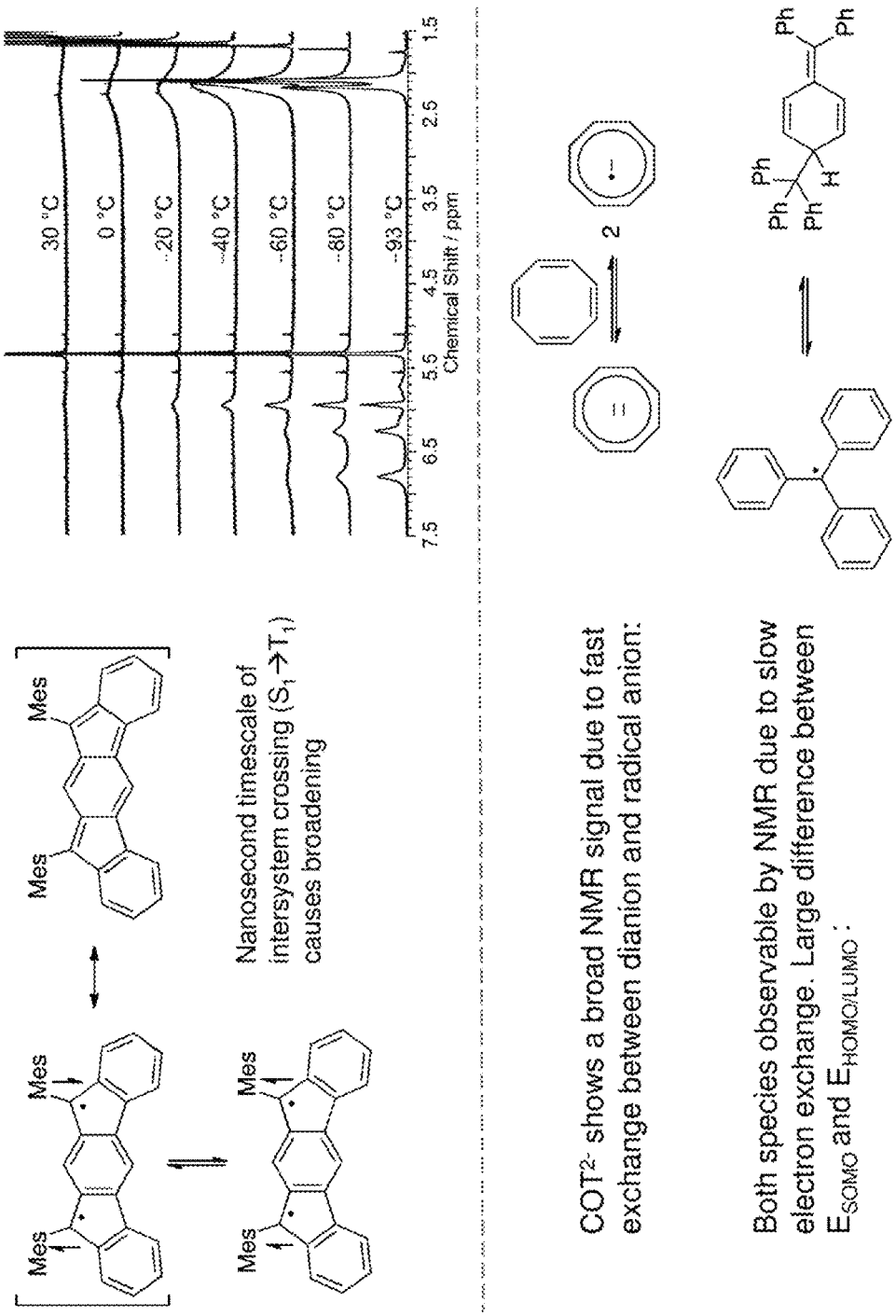
FIG. 5 shows NMR signal broadening.
Figure 6:
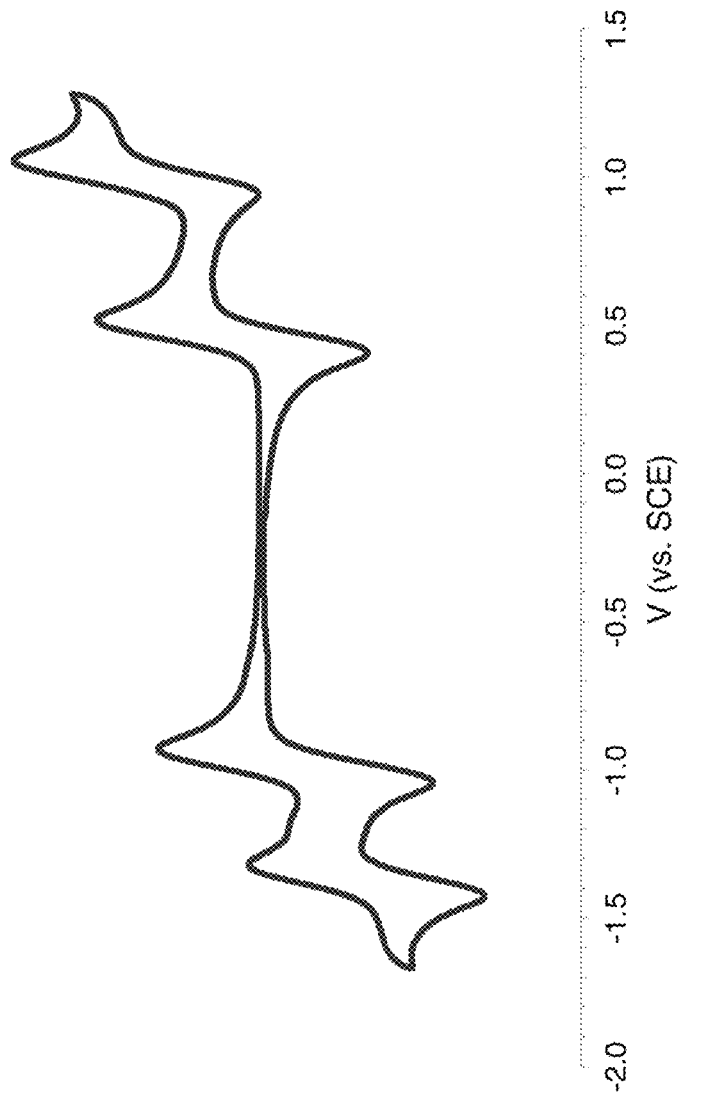
FIG. 6 shows cyclic voltammetry results.
Figure 7:
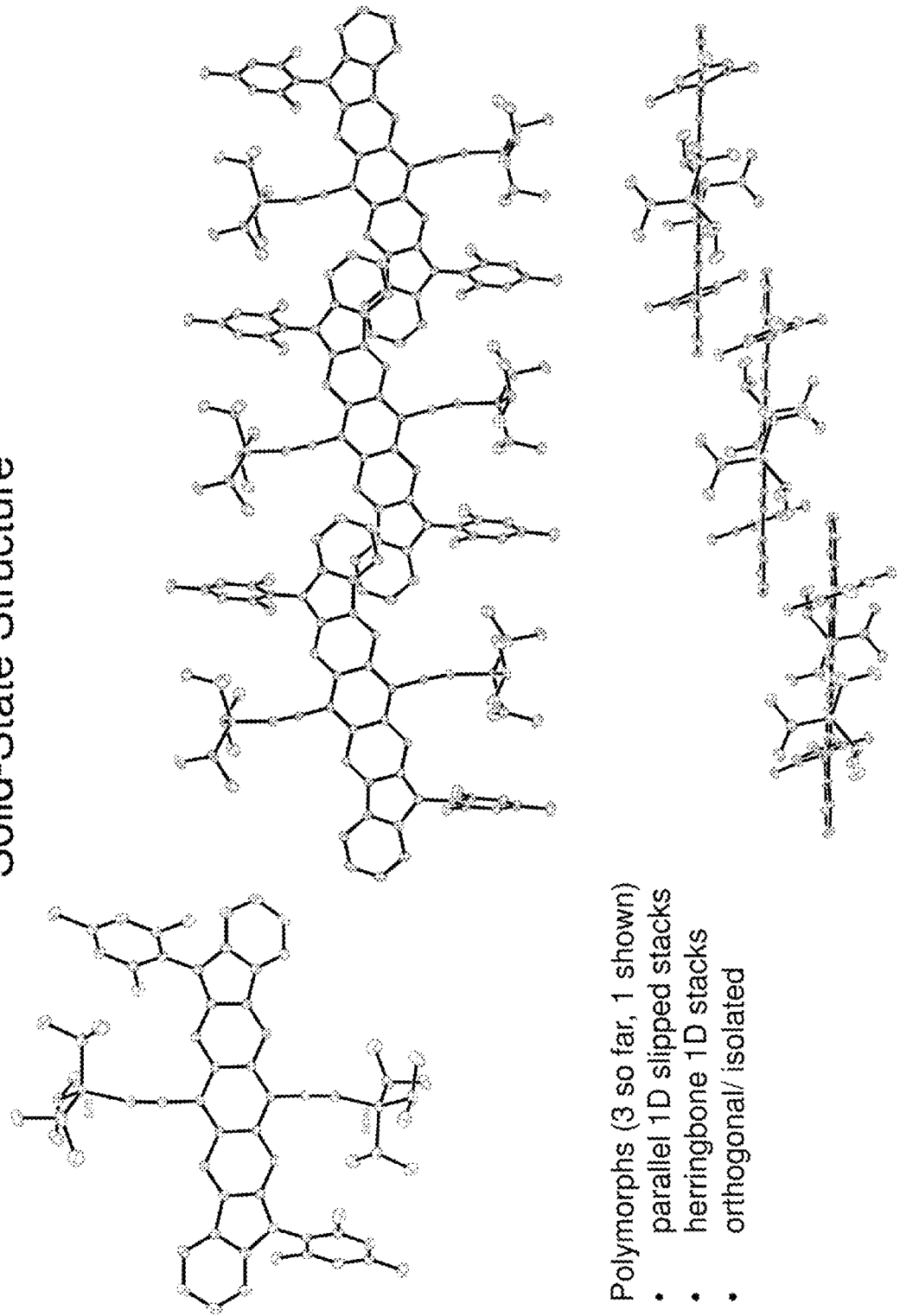
FIG. 7 shows solid-state structures.
Figure 8:
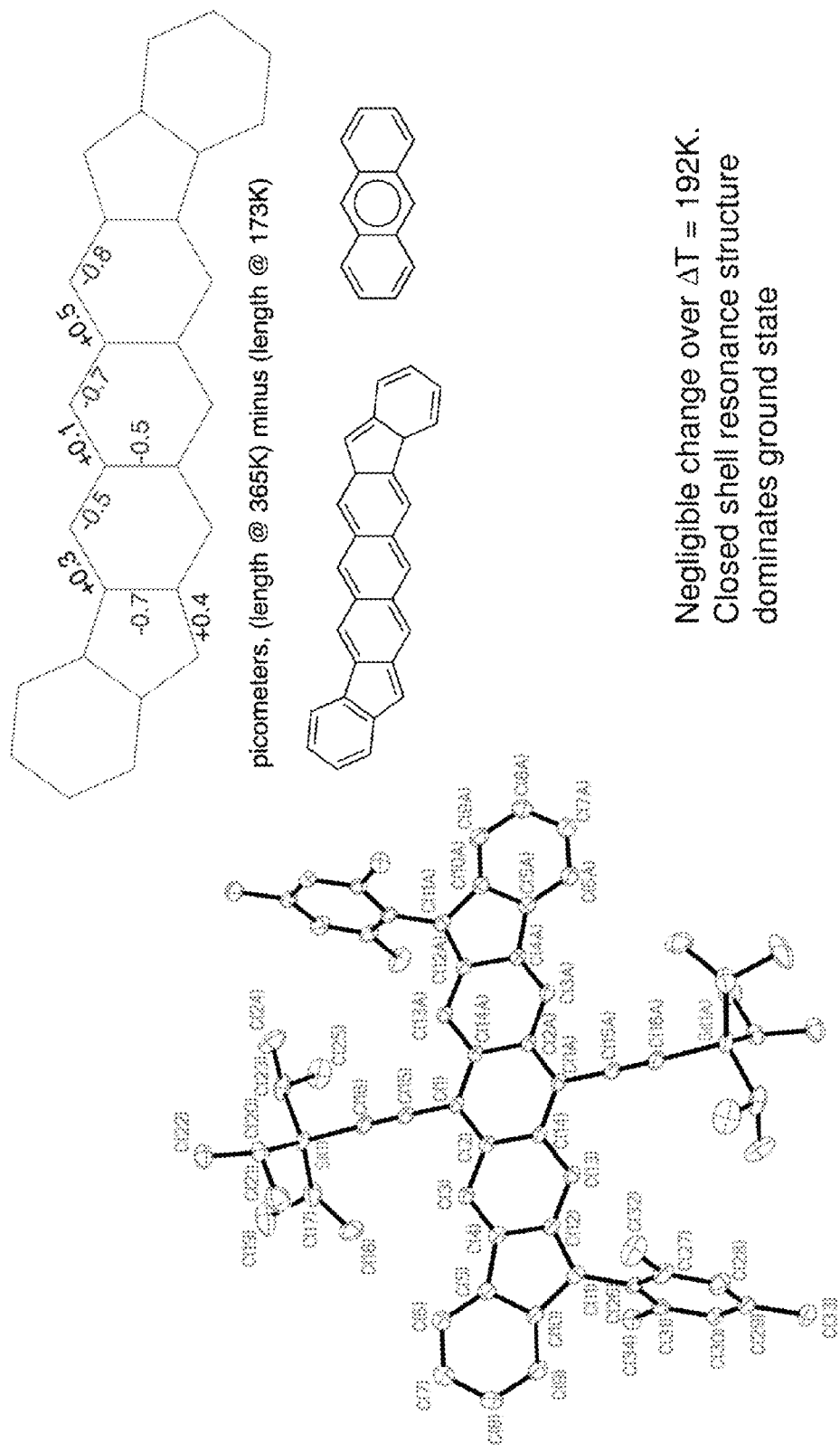
FIG. 8 shows single-crystal X-ray diffraction results.
Figure 9A:
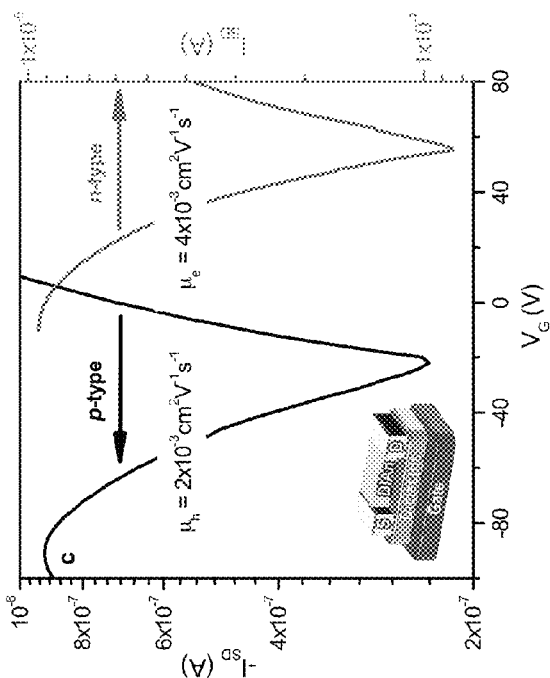
FIGS. 9A-9C show steady-state properties of DIAn (the final substituted diindenoanthracene product shown in Scheme 1 below) and OFET results.
Figure 9B:
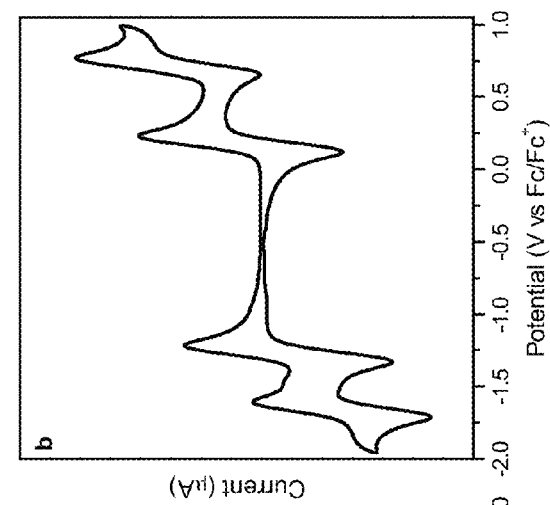
Figure 9C:
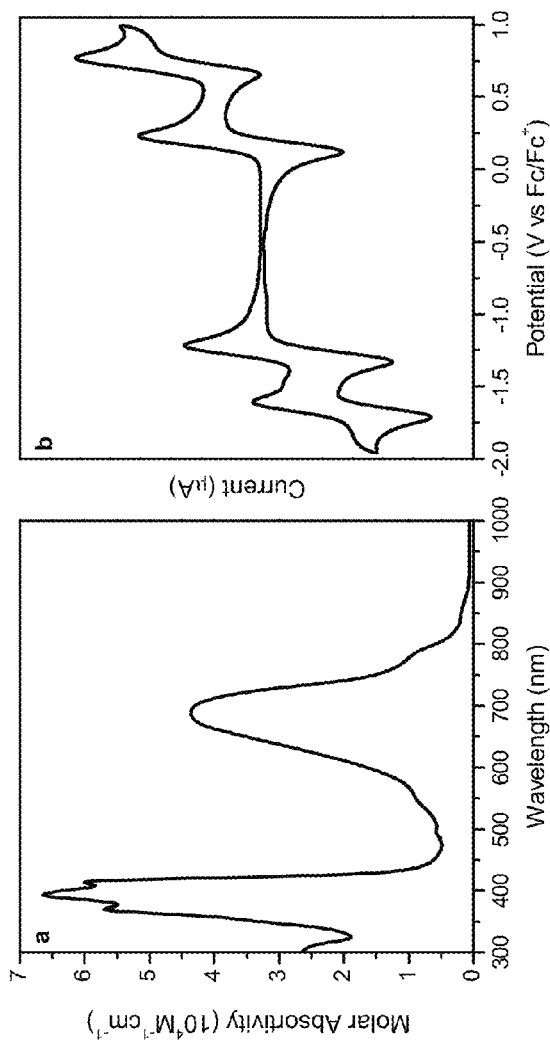
Figure 10B:
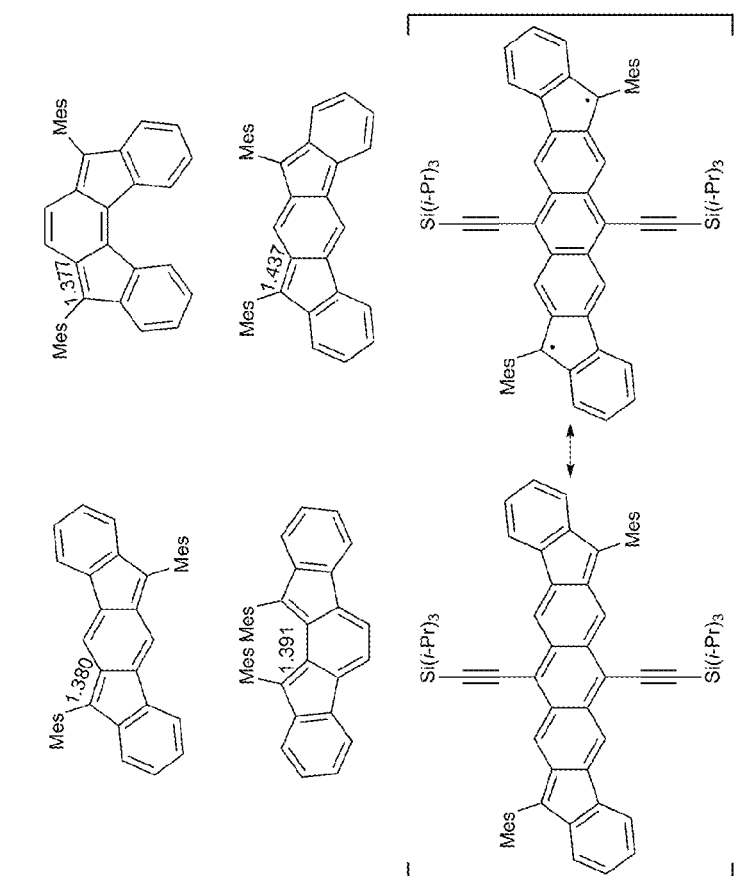
FIGS. 10A-10C show the solid-state structure of DIAn by single crystal X-ray diffraction.
Figure 10C:
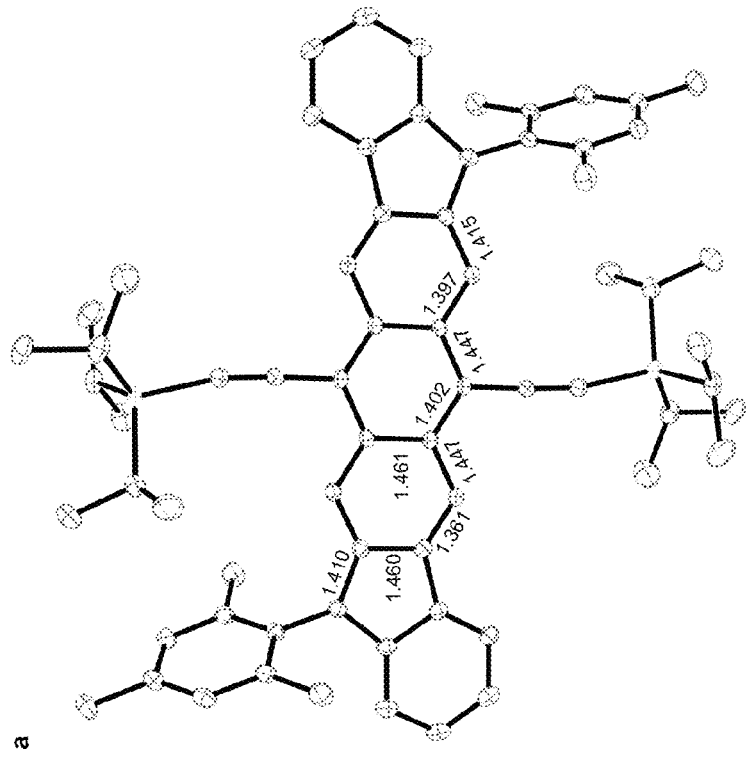
Figure 10A:
Figure 11C:
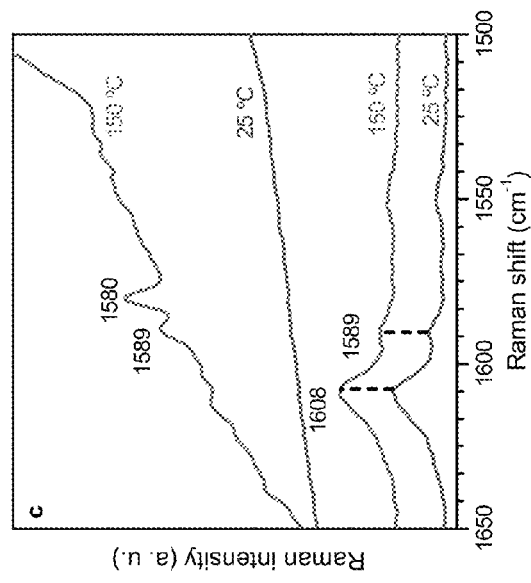
FIGS. 11A-11C show temperature dependent properties of DIAn.
Figure 11B:
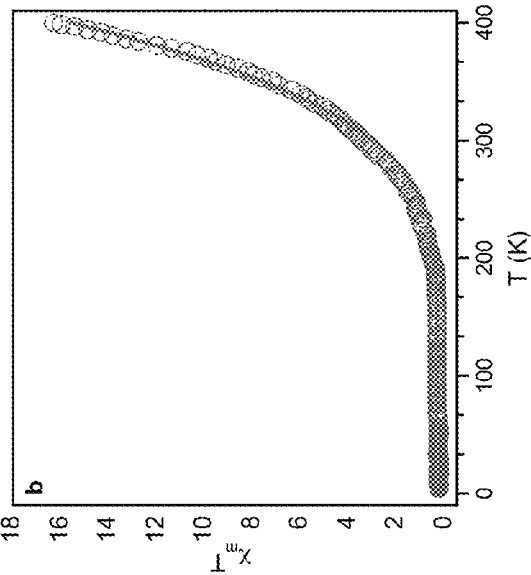
Figure 11A:
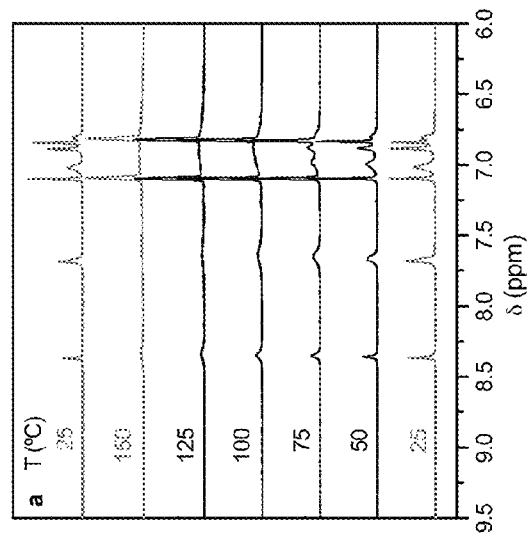
Figure 12A:
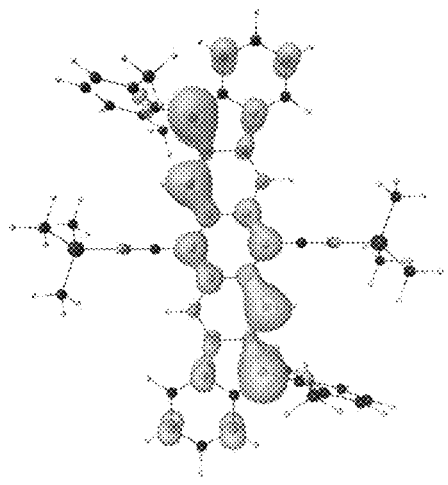
FIGS. 12A-12D show theoretical assessment of DIAn showing the open-shell nature.
Figure 12B:
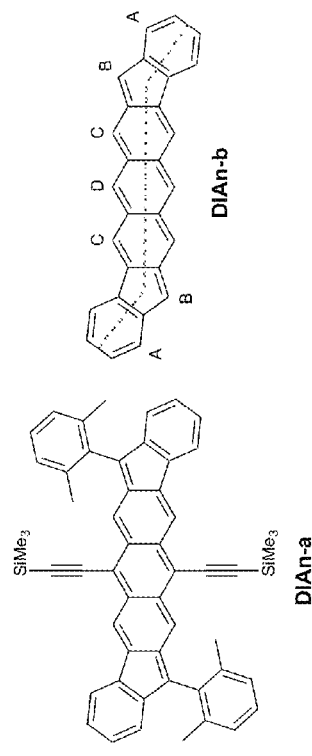
Figure 12D:
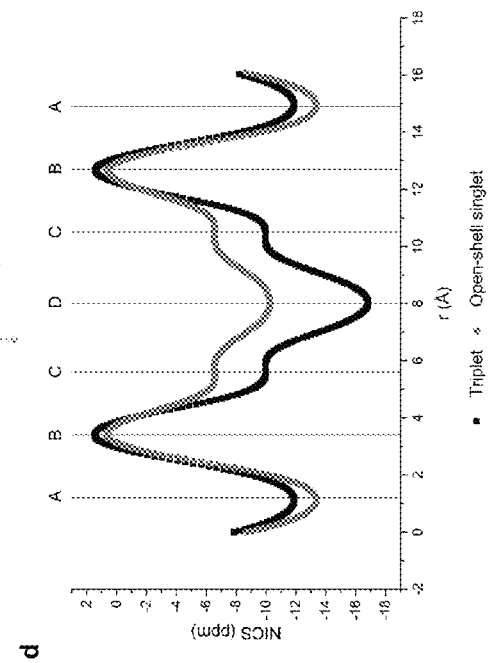
Figure 12C:
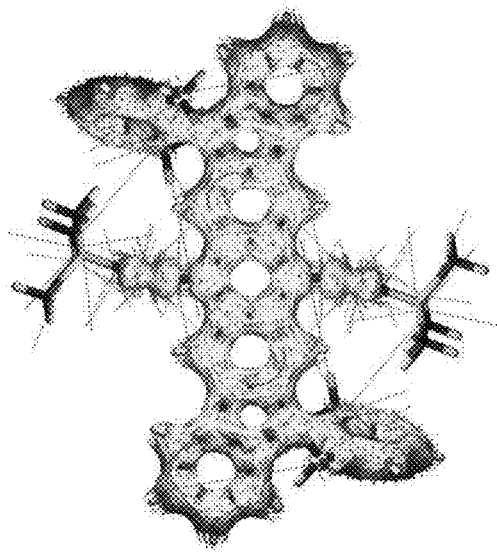

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Also, as used herein, the term "comprises" means "includes."

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkylaryl" refers to an aryl group having an alkyl group, as defined above, attached to the aryl group, as defined herein (—Ar—R), wherein Ar is an arylene group and R is an alkyl group.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "alkoxy" refers to a straight, branched or cyclic hydrocarbon configuration and combinations thereof, including from 1 to 20 carbon atoms, preferably from 1 to 10 carbon atoms, more preferably from 1 to 4 carbon atoms that include an oxygen atom at the point of attachment. An example of an "alkoxy group" is represented by the formula —OR, where R can be an alkyl group, optionally substituted with, e.g., an alkenyl, alkynyl, aryl, aralkyl, cycloalkyl, halogenated alkyl, or heterocycloalkyl group as described herein. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described herein.

The term "aralkyl" refers to an alkyl group that has at least one hydrogen atom replaced by an aryl group. An example of an aralkyl group is a benzyl group.

The term "aryl" refers to any carbon-based aromatic group including, but not limited to, phenyl, naphthyl, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like.

The term "heterocyclic" refers to mono or bicyclic rings or ring systems where at least one of the carbon atoms of the ring is substituted with a heteroatom such as, but not limited to, nitrogen, oxygen, sulfur, or phosphorous.

The term "heterocycloalkyl group" is a cycloalkyl group as defined above where at least one of the carbon atoms of the ring is substituted with a heteroatom such as, but not limited to, nitrogen, oxygen, sulfur, or phosphorous.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "silyl" refers to —SiR$_3$, wherein each R can be, independently, hydrogen or an alkyl, alkenyl, alkynyl, aryl, aralkyl, cycloalkyl, halogenated alkyl, or heterocycloalkyl group.

"Substituted" or "substitution" refers to replacement of a hydrogen atom of a molecule or an R-group with one or more additional R-groups. Unless otherwise defined, the term "substituted" or "substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$ cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, $arC_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl. The term "thioether" refers to a —S—R group, wherein R may be, for example, alkyl (including substituted alkyl), or aryl (including substituted aryl).

The term "thiol" refers to —SH. A "substituted thiol" refers to a —S—R group wherein R is not an aliphatic or aromatic group. For instance, a substituted thiol may be a halogenated thiol such as, for example, —$SF_5$.

The structural symbol —≡— designates an ethynyl group (i.e., —C≡C—).

Compounds

In one embodiment, the compounds have a structure represented by formula I:

Formula I

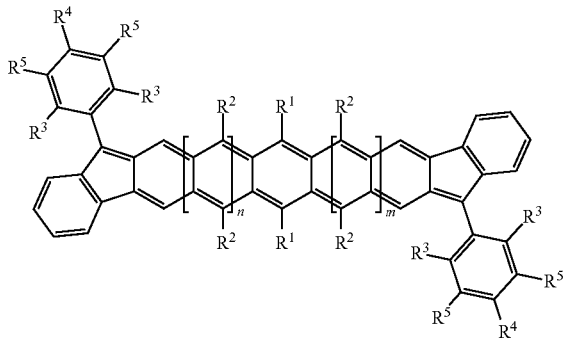

wherein each $R^1$ is independently H, alkynyl or substituted alkynyl;
each $R^2$ is independently H, alkynyl or substituted alkynyl;
each $R^3$ is independently alkyl or halogen (preferably methyl or F);
each $R^4$ is independently H, alkyl, or halogen (preferably H, methyl, tert-butyl, or F);
each $R^5$ is independently H or halogen (preferably F);
n is 0 or 1; and
m is 0 or 1, provided that if n is 0 then m is 0, and if n is 1 then m is 1.

In certain embodiments, the compounds have a structure represented by formula II (i.e., n and m of formula I are both 0):

Formula II

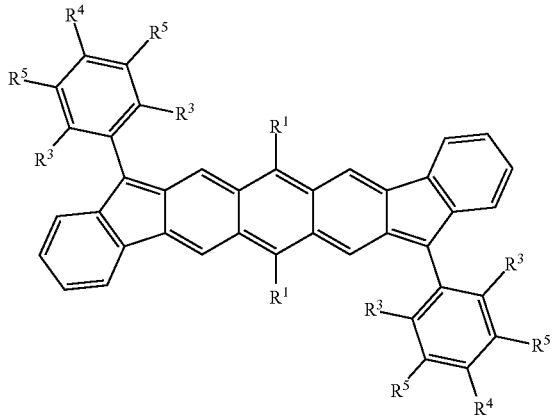

wherein $R^1$, $R^3$, $R^4$ and $R^5$ are the same as in formula I.

In certain embodiments of Formula 1 or 2, $R^1$ or $R^2$ are each an alkynyl or substituted alkynyl groups. In preferred embodiments of Formula 1 or 2, both $R^1$ groups or both $R^2$ groups are substituted alkynyls and are identical.

In a further embodiment, the compounds have a structure represented by formula III:

Formula III

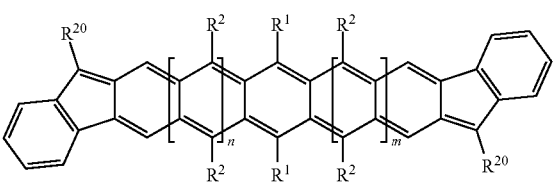

wherein each $R^1$ is independently H, alkynyl or substituted alkynyl;
each $R^2$ is independently H, alkynyl or substituted alkynyl;
each $R^{20}$ is independently aryl, substituted aryl, heterocyclic, substituted heterocyclic, alkenyl, substituted alkenyl, alkynyl, or substituted alkynyl;
n is 0 or 1; and
m is 0 or 1, provided that if n is 0 then m is 0, and if n is 1 then m is 1.

In certain embodiments, the compounds have a structure represented by formula IV (i.e., n and m of formula III are both 0):

Formula IV

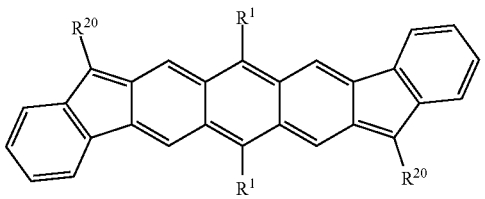

wherein $R^1$ and $R^{20}$ are the same as in formula III.

In a further embodiment, the compounds have a structure represented by formula V:

Formula V

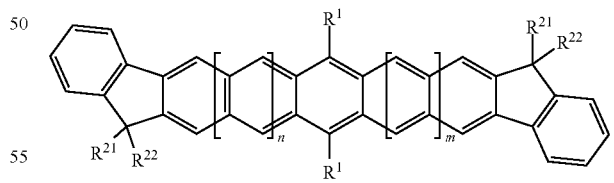

wherein each $R^1$ is independently H, alkynyl or substituted alkynyl;
each $R^{21}$ and $R^{22}$ is independently aryl, substituted aryl, heterocyclic, or substituted heterocyclic,
n is 0 or 1; and
m is 0 or 1, provided that if n is 0 then m is 0, and if n is 1 then m is 1.

In certain embodiments, the compounds have a structure represented by formula VI (i.e., n and m of formula V are both 0):

Formula VI

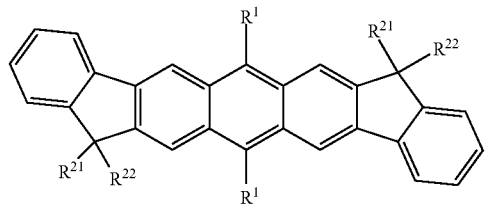

wherein $R^1$, $R^{21}$ and $R^{22}$ are the same as in formula V.

In a further embodiment, the compounds have a structure represented by formula VII:

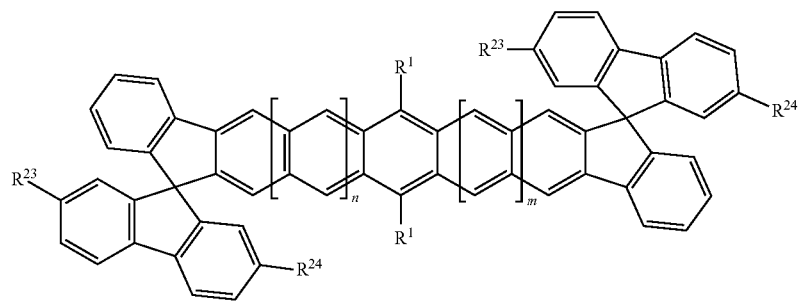

wherein each $R^1$ is independently H, alkynyl or substituted alkynyl;

each $R^{23}$ and $R^{24}$ is independently aryl, substituted aryl, heterocyclic, or substituted heterocyclic, n is 0 or 1; and m is 0 or 1, provided that if n is 0 then m is 0, and if n is 1 then m is 1.

In certain embodiments, the compounds have a structure represented by formula VIII (i.e., n and m of formula V are both 0):

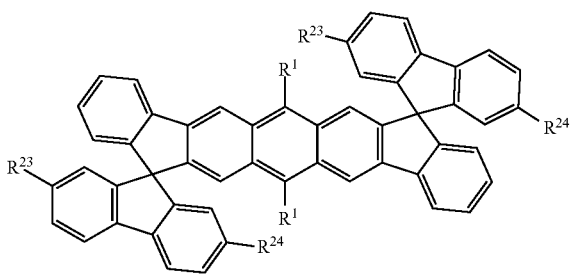

wherein $R^1$, $R^{23}$ and $R^{24}$ are the same as in formula VII.

In certain embodiments of formulae I-VIII, the alkynyl or substituted alkynyl may be a $C_2$-$C_{10}$, more particularly $C_2$-$C_5$, alkynyl or substituted alkynyl (e.g., —C≡CR). In preferred embodiments, the alkynyl or substituted alkynyl is ethynyl or substituted ethynyl. The substituted alkynyl may be substituted with a silyl-containing group, a hydrocarbyl derivative of a silyl group such as an alkyl silyl (particularly tri-$C_1$-$C_6$ alkylsilyls), an aryl silyl (particularly tri-arylsilyls), or an alkoxy silyl (particularly tri-$C_1$-$C_6$ alkoxysilyls), a tin-containing group, or a germanium-containing group. Illustrative substituents for the substituted alkynyl include —Si(isopropyl)$_3$ (i.e., "TIPS"), —Si(n-propyl)$_3$, —Si(n-butyl)$_3$, —Si(isobutyl)$_3$, —Si(tert-butyl)$_3$, —Si(sec-butyl)$_3$, —Si(ethyl)$_3$, —Si(methyl)$_3$, —Si(tert-butyl)(methyl)$_2$, —Si(c-pentyl)$_3$, —Si(c-hexyl)$_3$, —Si(phenyl)$_3$, —Si(Si(methyl)$_3$)$_3$. Particularly preferred for $R^1$ or $R^2$ is (trialkylsilyl)alkynyl, preferably (trialkylsilyl)ethynyl.

For example, in certain embodiments, $R^1$ or $R^2$ is:

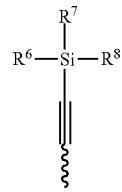

wherein each $R^6$, $R^7$, and $R^8$ is independently alkyl or silyl (preferably —CH(CH$_3$)$_2$, —C(CH$_3$)$_3$, —Si(CH$_3$)$_3$, or —(CH$_2$)$_7$CH$_3$. In certain embodiments, $R^6$, $R^7$, and $R^8$ are identical groups.

In certain embodiments, each $R^3$ group is identical.
In certain embodiments, each $R^4$ group is identical.
In certain embodiments, each $R^5$ group is identical.
In certain embodiments, $R^3$ and $R^4$ are each methyl, and $R^5$ is H.
In certain embodiments, $R^3$ and $R^4$ are identical.
In certain embodiments, $R^3$ and $R^4$ are identical, and $R^3$ and $R^4$ are not H.
In certain embodiments, each $R^{20}$ is independently =C($R^{30}$)$_2$ wherein each $R^{30}$ is independently cyano or alkoxycarbonyl (e.g., =C(CN)(CO$_2$R), or C($R^{30}$)$_2$ together forms part of a dithiolyl ring or substituted dithiolyl ring (i.e., each $R^{30}$ is —S—). In certain embodiments, the dithiolyl ring is di-substituted with thiol or substituted thiol.

The compounds disclosed herein typically include two types of stabilizing groups. For example, the bulky —Ar$R^3R^4R^5$ groups (e.g., a mesityl group) block sites of high-spin density on the cyclopenta-fused rings. The $R^1$ or $R^2$ groups (e.g., triisopropylsilylacetylene groups) are sterically bulky to prevent intermolecular decomposition pathways as well as electron-withdrawing to aid in oxygen stability. Thus, there groups help prevent inter-molecular reactions of the biradical compounds.

Also disclosed herein are dimers or trimers having the following structures:

Synthesis of diindenoanthracene compounds disclosed herein begins with Suzuki cross-coupling between dibromoanthracene and 2-formylbenzene boronic acid (Scheme 1 below). Buchwald's SPhos ligand was critical for the efficient coupling of the electron-poor, ortho-substituted arylboronic acid. Next, addition of mestiylmagnesium bromide gives the diol as a mixture of diastereomers in quantitative yield. Intramolecular Friedel-Crafts type alkylation of the anthracene core with boron trifluoride as the catalyst proceeds in good yield. Closure to the 1-position of anthracene was not observed, most likely due to the steric repulsion of the bulky mesityl group and the (tri-isopropylsilyl)acetylene. Finally, oxidation with DDQ at elevated temperature gives the fully conjugated diindenoanthracene (designated "DIAn"). The synthesis has four steps from known compounds, requires no chromatography, and the DIAn product is stable in degassed solutions.

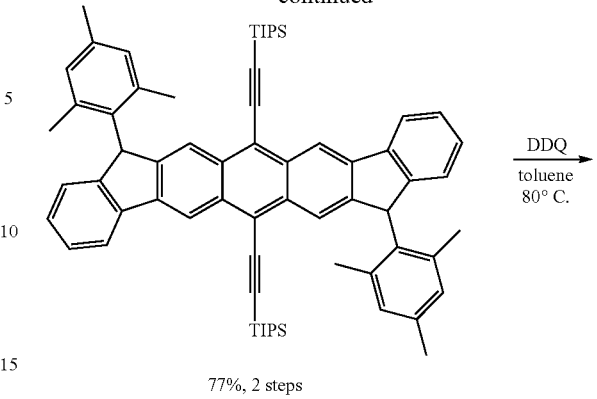

Scheme 1. Synthesis of Diindenoanthrancene.

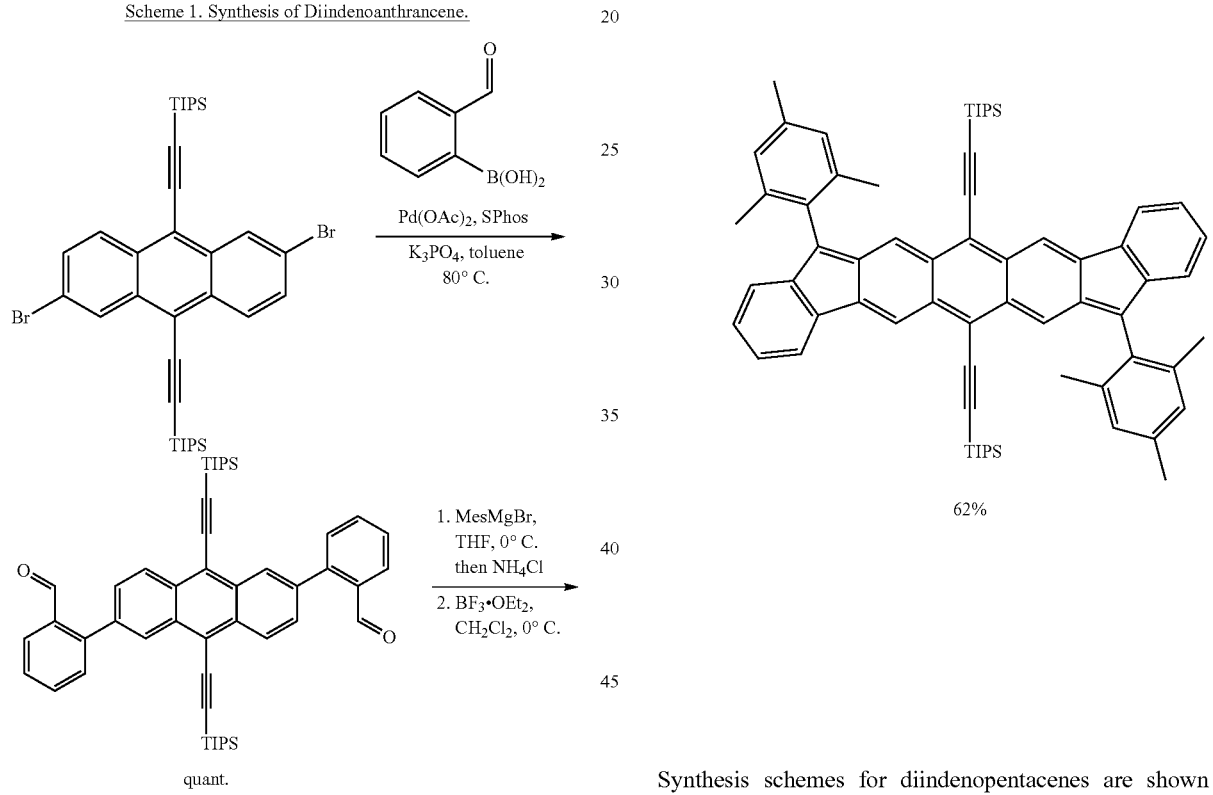

Synthesis schemes for diindenopentacenes are shown below.

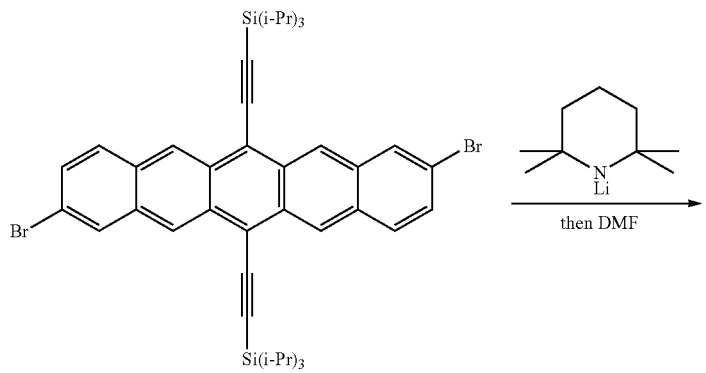

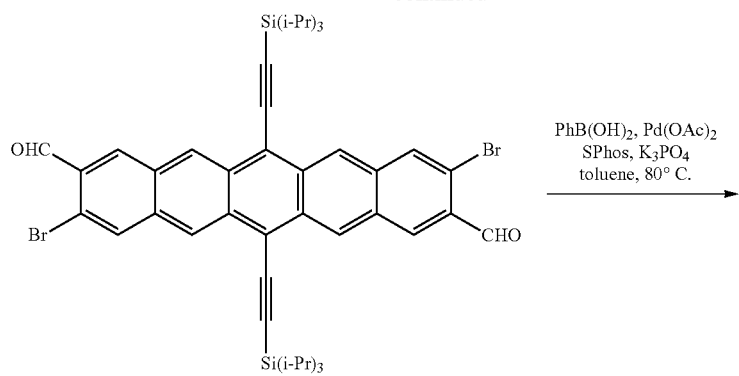
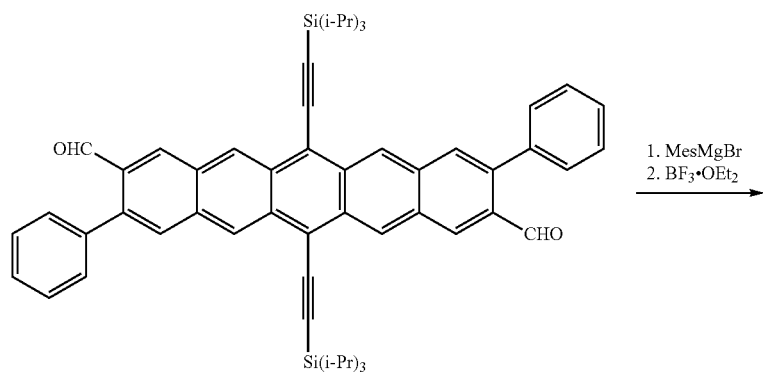
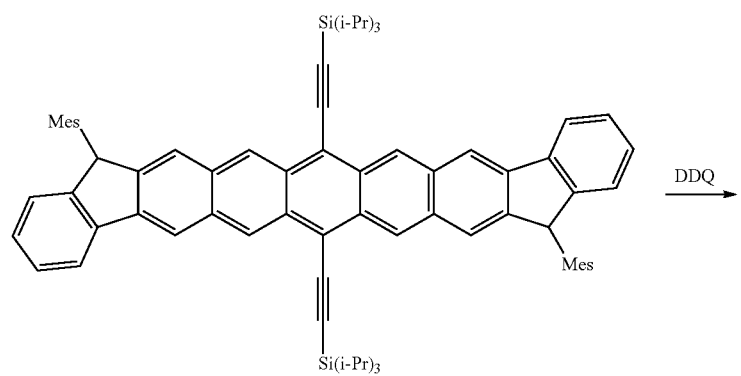
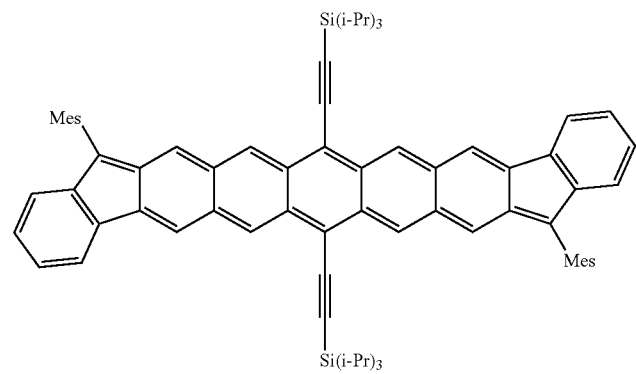

-continued
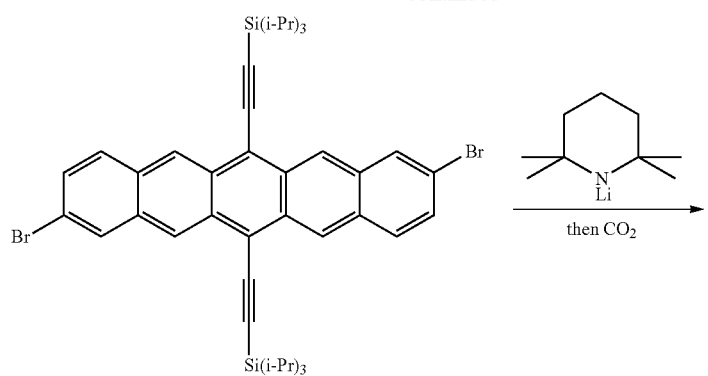
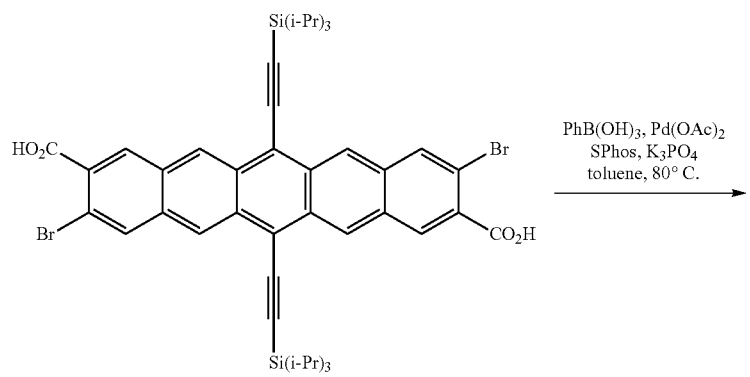
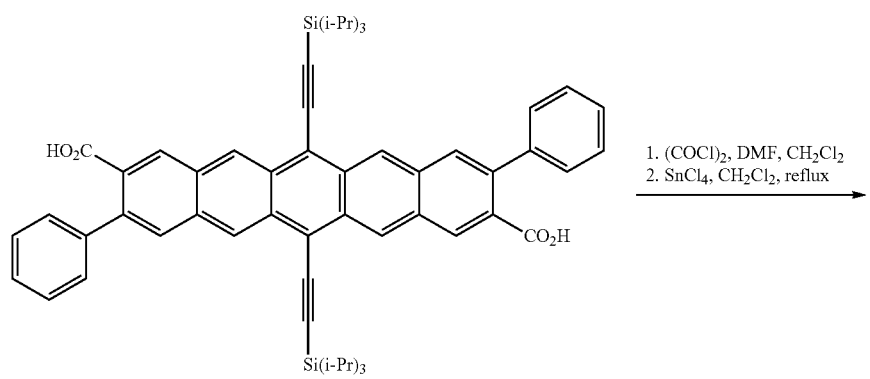
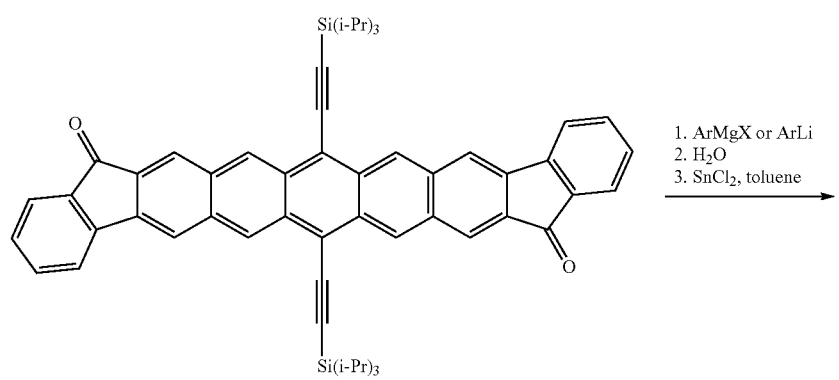

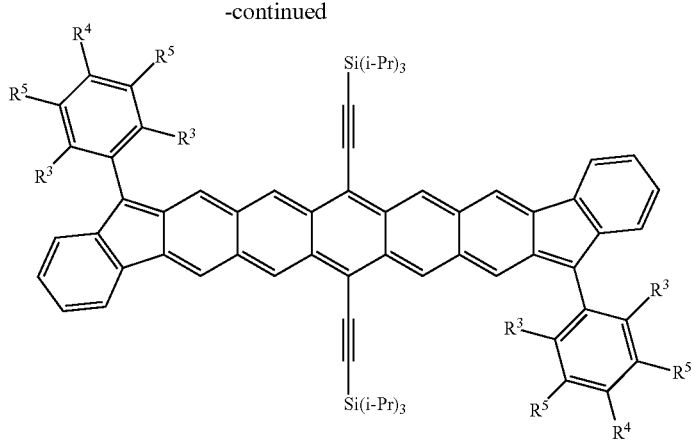
A further synthesis scheme for diindenoanthracene compounds is shown below.
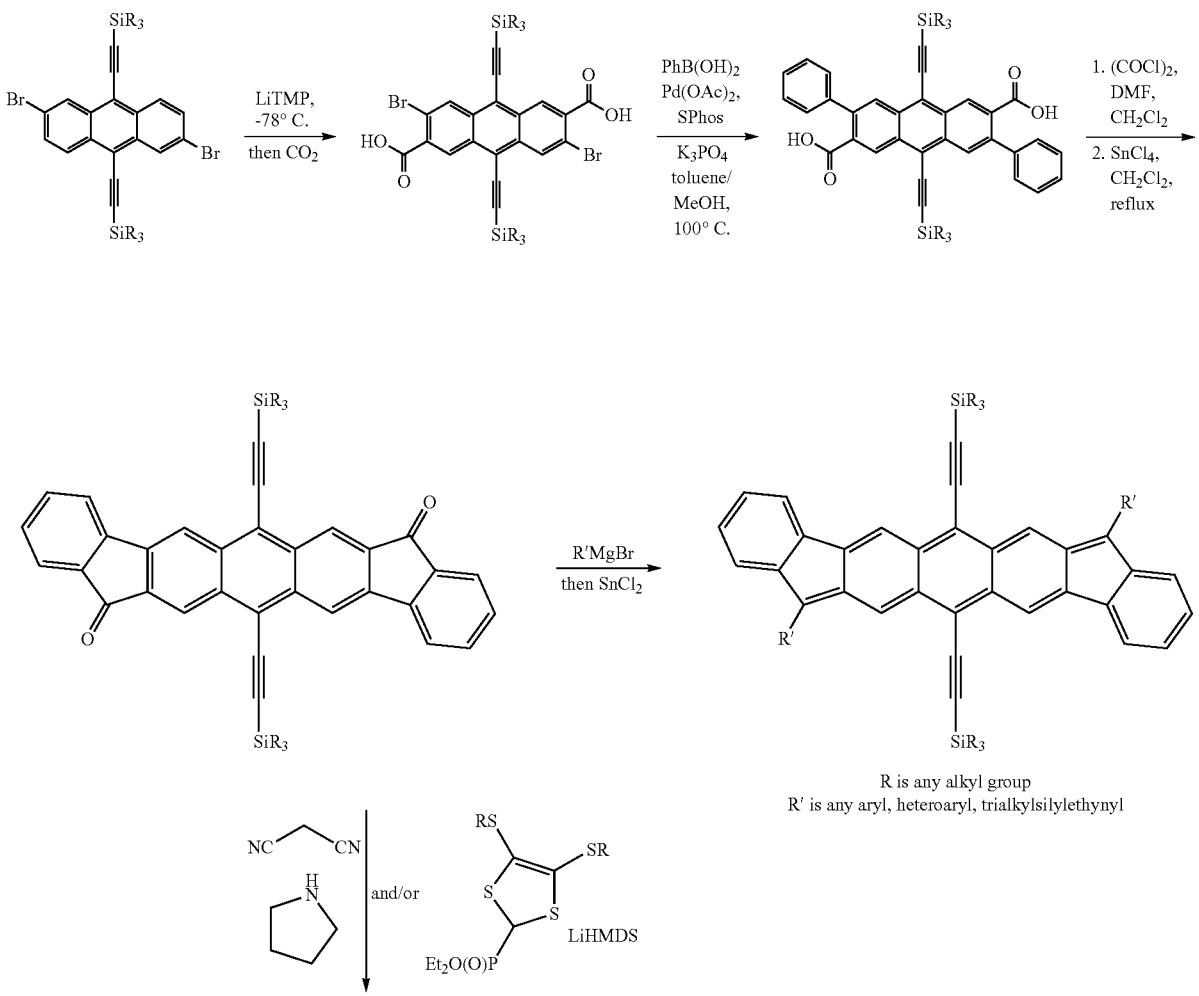

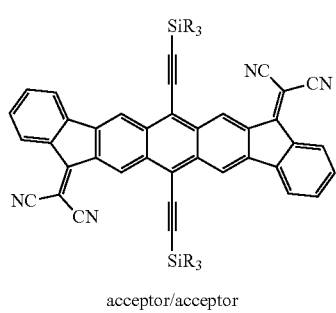

acceptor/acceptor

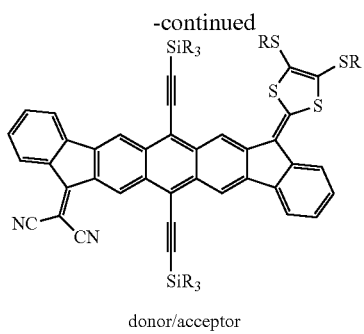

donor/acceptor

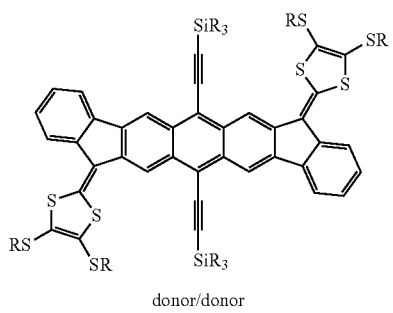

donor/donor

Another synthesis scheme for diindenoanthracene compounds is shown below.

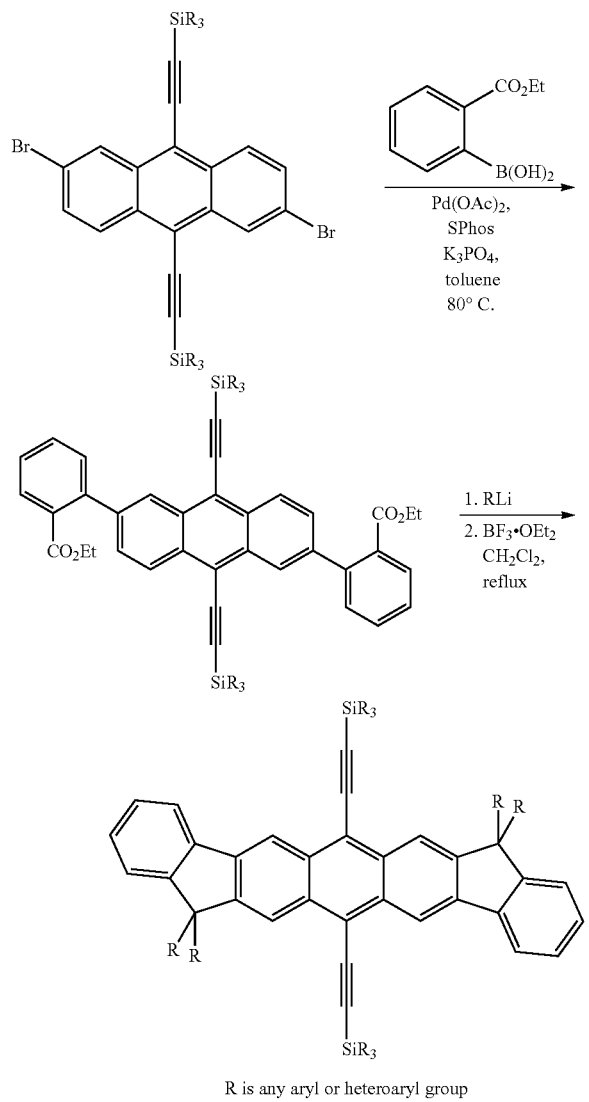

R is any aryl or heteroaryl group

The compounds disclosed herein feature a mild biradical character and have the potential for singlet fission in organic photovoltaics and applications in organic spin electronics. It has been found that expanding an indenofluorene core results in an electrochemical gap of 1.45 eV and near-IR absorption. Single crystal X-ray diffraction reveals a singlet biradical ground state involving a 2,6-anthraquinodimethane resonance structure. Variable temperature NMR and computational studies indicate the presence of a thermally accessible triplet state. Air and solution stability is afforded by stabilization of reactive sites by the bulky (triisopropylsilyl) ethynyl and mesityl groups. The present inventors have also recognized that the excited state lifetimes increase as the core size (number of fused conjugated 6-member rings) increases.

DIAn was assessed for potential application in organic photovoltaics. Diradicals are reactive species that are typically difficult to characterize by traditional methods. The pure compound exhibits well-resolved $^1$H NMR spectra at −25° C. in deoxygenated $CD_2Cl_2$. Heating to 150° C. in 1,2-dichlorobenzene-d4 results in broadening and finally loss of signal. This could arise from a thermally accessible triplet biradical state or another process involving fast electron exchange at elevated temperature. This result is significant as the parent structure was predicted to have ~68% contribution of the open shell form to the ground state by DFT calculations.

Compound Applications

The compounds disclosed herein may be used in electronic or electrooptical devices such as, for example, an organic light-emitting diode (OLED), an organic field-effect transistor OFET), or an organic photovoltaic cell (OPV). The compounds disclosed herein may be used as organic semiconductors in form of thin organic layers or films, for example, less than 30 microns thick. For instance, the semiconducting layer is at most 1 micron thick, although it may be thicker if required. For various electronic device applications, the thickness may also be less than about 1 micron thick. For use in an OFET, the layer thickness may typically be 500 nm or less, in an OLEDs be 100 nm or less. The exact thickness of the layer will depend, for example, upon the requirements of the electronic device in which the layer is used.

For example, the active semiconductor channel between the drain and source in an OFET may comprise a layer that includes the compound disclosed herein. As another example, a hole injection or transport layer, and or an electron blocking layer in an OLED device may comprise a layer that includes the compound disclosed herein.

An OFET may comprise: a source electrode, a drain electrode, a gate electrode, a semiconducting layer, one or more gate insulator layers, optionally a substrate, wherein the semiconductor layer comprises one or more compound as described herein.

In certain embodiments the photovoltaic cell includes an anode, a cathode, and a semiconductor layer or film that includes at least one of the compounds disclosed herein.

Several embodiments are described below in the following numbered paragraphs:

1. A compound having a structure represented by formula I:

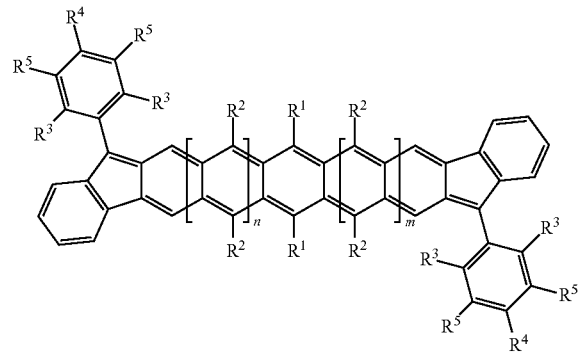

Formula I wherein each $R^1$ is independently H, alkynyl or substituted alkynyl;
each $R^2$ is independently H, alkynyl or substituted alkynyl;
each $R^3$ is independently alkyl or halogen;
each $R^4$ is independently H, alkyl, or halogen;
each $R^5$ is independently H or halogen;
n is 0 or 1; and
m is 0 or 1, provided that if n is 0 then m is 0, and if n is 1 then m is 1.

2. The compound of paragraph 1, wherein the compound has a structure represented by formula II:

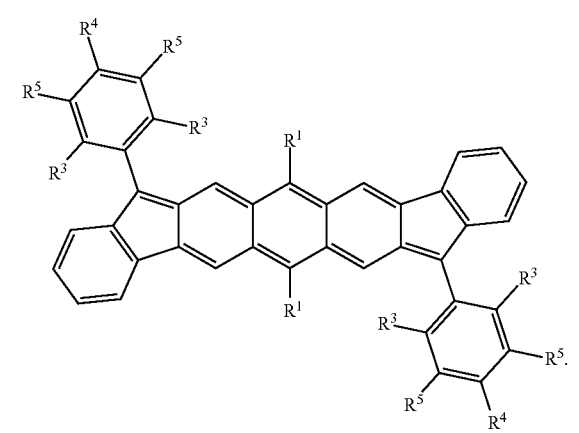

Formula II

3. The compound of paragraph 1 or 2, wherein both $R^1$ groups or both $R^2$ groups are substituted alkynyls and are identical.

4. The compound of any one of paragraphs to 1 to 3, wherein the substituted alkynyl is a substituted ethynyl.

5. The compound of paragraph 4, wherein the substituted ethynyl is a silyl-substituted ethynyl.

6. The compound of paragraph 1 or 2, wherein both $R^1$ groups or both $R^2$ groups are (trialkylsilyl)ethynyls and are identical.

7. The compound of paragraph 1 or 2, wherein both $R^1$ groups or both $R^2$ groups are

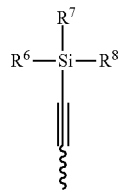

wherein each $R^6$, $R^7$, and $R^8$ is independently alkyl or silyl, and both $R^1$ groups or both $R^2$ groups are identical.

8. The compound of paragraph 7, wherein $R^6$, $R^7$, and $R^8$ are each independently selected from —CH(CH$_3$)$_2$, —C(CH$_3$)$_3$, —Si(CH$_3$)$_3$, or —(CH$_2$)$_7$CH$_3$.

9. The compound of any one of paragraphs 1 to 8, wherein each $R^3$ group is identical.

10. The compound of any one of paragraphs 1 to 9, wherein each $R^4$ group is identical.

11. The compound of any one of paragraphs 1 to 10, wherein each $R^5$ group is identical.

12. The compound of paragraph 1 or 2, wherein $R^3$ and $R^4$ are each methyl, and $R^5$ is H.

13. The compound of any one of paragraphs 1 to 11, wherein $R^3$ is methyl or F.

14. The compound of any one of paragraphs 1 to 11 or 13, wherein $R^4$ is methyl, tert-butyl, or F.

15. The compound of any one of paragraphs 1 to 11, 13 or 14, wherein $R^5$ is F.

16. An electronic or electrooptical device that includes the compound of paragraph 1.

In view of the many possible embodiments to which the principles of the disclosed invention may be applied, it should be recognized that the illustrated embodiments are only preferred examples of the invention and should not be taken as limiting the scope of the invention.

What is claimed is:

1. A compound having a structure corresponding to formula I:

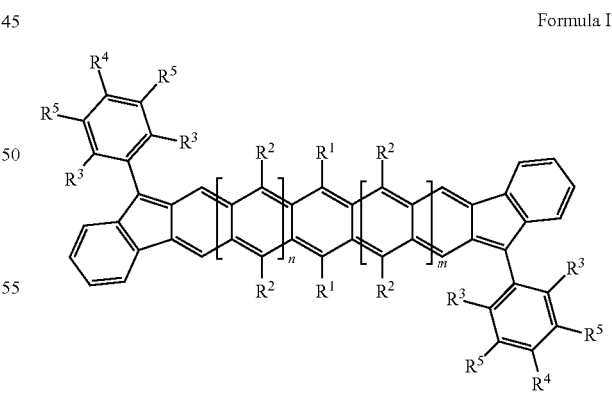

Formula I wherein each $R^1$ is independently H, alkynyl or substituted alkynyl;
each $R^2$ is independently H, alkynyl or substituted alkynyl;
each $R^3$ is independently alkyl or halogen;
each $R^4$ is independently H, alkyl, or halogen;
each $R^5$ is independently H or halogen;

n is 0 or 1; and m is 0 or 1, provided that if n is 0 then m is 0, and if n is 1 then m is 1.

2. The compound of claim 1, wherein the compound has a structure corresponding to formula II:

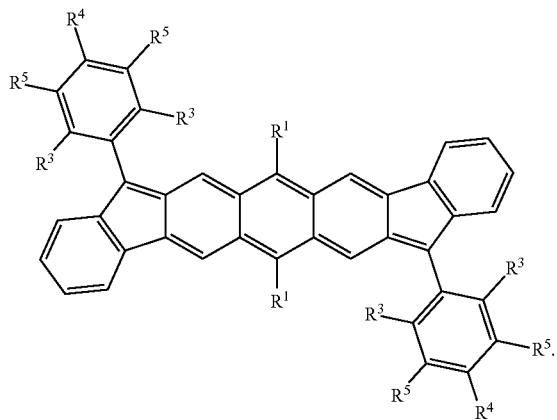

Formula II

3. The compound of claim 1, wherein both $R^1$ groups or both $R^2$ groups are substituted alkynyls and are identical.

4. The compound of claim 1, wherein the substituted alkynyl is a substituted ethynyl.

5. The compound of claim 4, wherein the substituted ethynyl is a silyl-substituted ethynyl.

6. The compound of claim 1, wherein both $R^1$ groups or both $R^2$ groups are (trialkylsilyl)ethynyls and are identical.

7. The compound of claim 1, wherein both $R^1$ groups or both $R^2$ groups are

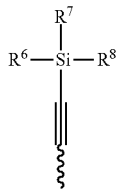

wherein each $R^6$, $R^7$, and $R^8$ is independently alkyl or silyl, and both $R^1$ groups or both $R^2$ groups are identical.

8. The compound of claim 7, wherein $R^6$, $R^7$, and $R^8$ are each independently selected from —CH(CH$_3$)$_2$, —C(CH$_3$)$_3$, —Si(CH$_3$)$_3$, or —(CH$_2$)$_7$CH$_3$.

9. The compound of claim 1, wherein each $R^3$ group is identical.

10. The compound of claim 1, wherein each $R^4$ group is identical.

11. The compound of claim 1, wherein each $R^5$ group is identical.

12. The compound of claim 1, wherein $R^3$ and $R^4$ are each methyl, and $R^5$ is H.

13. The compound of claim 1, wherein $R^3$ is methyl or F.

14. The compound of claim 1, wherein $R^4$ is methyl, tert-butyl, or F.

15. The compound of claim 1, wherein $R^5$ is F.

16. An electronic or electrooptical device that includes the compound of claim 1.

17. A compound having a structure corresponding to formula III:

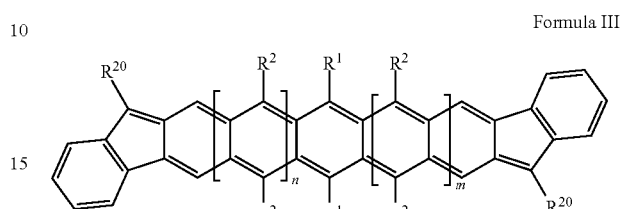

Formula III wherein each $R^1$ is independently H, alkynyl or substituted alkynyl;

each $R^2$ is independently H, alkynyl or substituted alkynyl;

each $R^{20}$ is independently aryl, substituted aryl, heterocyclic, substituted heterocyclic, alkenyl, substituted alkenyl, alkynyl, or substituted alkynyl;

n is 0 or 1; and m is 0 or 1, provided that if n is 0 then m is 0, and if n is 1 then m is 1.

18. The compound of claim 17, wherein the compound has a structure corresponding to formula IV:

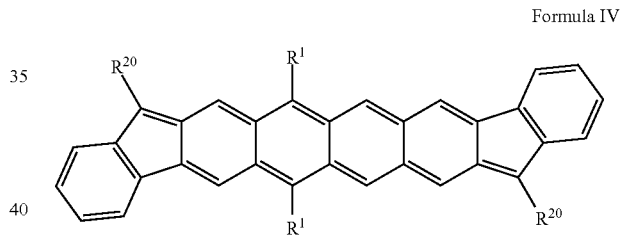

Formula IV wherein $R^1$ and $R^{20}$ are the same as in formula III.

19. The compound of claim 18, wherein each $R^{20}$ is independently =C(R$^{30}$)$_2$ wherein each $R^{30}$ is independently cyano or alkoxycarbonyl, or C(R$^{30}$)$_2$ together forms part of a dithiolyl ring or substituted dithiolyl ring.

20. An electronic or electrooptical device that includes the compound of claim 18.

21. The compound of claim 4, wherein the substituted ethynyl is a Si(methyl)$_3$-substituted ethynyl.

22. The compound of claim 4, wherein the substituted ethynyl is a Si(isopropyl)$_3$-substituted ethynyl.

23. The compound of claim 21, wherein $R^3$ and $R^4$ are each methyl, and $R^5$ is H.

24. The compound of claim 2, wherein the substituted alkynyl is a Si(methyl)$_3$-substituted ethynyl.

25. The compound of claim 2, wherein the substituted alkynyl is a Si(isopropyl)$_3$-substituted ethynyl.

* * * * *